United States Patent

Dietl

[11] Patent Number: 5,985,335
[45] Date of Patent: Nov. 16, 1999

[54] AGENT FOR ACTING UPON BONE FORMATION DISTURBANCES CONTAINING ALKALINE CITRATES, LACTATES AND/OR MALATES

[75] Inventor: Hans Dietl, Bad Aibling, Germany

[73] Assignee: Orthomol Pharmazeutische Vertriebs GmbH, Langenfeld, Germany

[21] Appl. No.: 08/875,381

[22] PCT Filed: Dec. 20, 1995

[86] PCT No.: PCT/EP95/05049

§ 371 Date: Nov. 28, 1997

§ 102(e) Date: Nov. 28, 1997

[87] PCT Pub. No.: WO96/23504

PCT Pub. Date: Aug. 8, 1996

[30] Foreign Application Priority Data

Feb. 1, 1995 [DE] Germany .......................... 195 03 190

[51] Int. Cl.⁶ .......................... A61K 33/36; A61K 33/06; A61K 33/00; A61K 31/59
[52] U.S. Cl. .......................... 424/610; 424/629; 424/682; 514/167
[58] Field of Search .......................... 514/167; 424/629, 424/610, 682

[56] References Cited

U.S. PATENT DOCUMENTS

| 5,389,391 | 2/1995 | Monte | 426/335 |
| 5,780,451 | 7/1998 | DeMichele et al. | 514/54 |

FOREIGN PATENT DOCUMENTS

| 0 183 527 A2 | 4/1986 | European Pat. Off. . |
| 0 335 140 A1 | 4/1989 | European Pat. Off. . |
| 0 390 930 A1 | 10/1990 | European Pat. Off. . |
| 0 507 157 A1 | 7/1992 | European Pat. Off. . |
| 0 704 199 A1 | 3/1996 | European Pat. Off. . |
| 2 704 393 | 4/1994 | France . |
| 25 30 372 A1 | 11/1977 | Germany . |
| 37 20510 A1 | 7/1988 | Germany . |
| 195 03 190 | 2/1995 | Germany . |
| 52 01 8811 | 2/1977 | Japan . |
| 52 13763 | 8/1993 | Japan . |
| WO 92/19251 | 11/1992 | WIPO . |
| WO 92/21355 | 12/1992 | WIPO . |

OTHER PUBLICATIONS

J.T. Monte Neto et al., "Osteomalacia Secondary To Renal Tubular Acidosis In A Patient With Primary Sjogren's Syndrome", *Clinical and Experimental Rheumatology*, 9:625–627, 1991.

Yukihara Okamoto et al., "The Effects Of Vitamin K1 and K2 on Parathyroid Hormone Secretion", Wakayama Med. Rep., 26, 95–101, 1983.

CA: 113; 52548f—Morris et al, 1990.

*Primary Examiner*—Theodore J. Criares
*Attorney, Agent, or Firm*—Burns, Doane, Swecker & Mathis, L.L.P.

[57] ABSTRACT

The invention relates to an agent for the prophylaxis and/or therapy of conditions associated with a disorder of bone formation. It contains alkali metal citrates and/or alkali metal lactates and/or alkali metal malates, optionally together with one or more active substances selected from vitamin K, calcium salts and vitamin D. The agent preferably contains potassium citrates and/or sodium citrates or potassium lactates and/or sodium lactates and serves for the prophylaxis and/or therapy of osteoclasis, in particular osteoporosis or osteomalacia.

18 Claims, No Drawings

AGENT FOR ACTING UPON BONE FORMATION DISTURBANCES CONTAINING ALKALINE CITRATES, LACTATES AND/OR MALATES

This application is a rule 371 of PCT/EP 95/05049 filed Dec. 20, 1995.

FIELD OF THE INVENTION

The invention relates to an agent for the prophylaxis and/or therapy of conditions associated with a disorder of bone formation.

BACKGROUND OF THE INVENTION

Disorders of bone metabolism, in particular in the form of the occurrence of osteoporosis, are widespread in Western industrial countries. Osteoporosis is a disease which is characterised by disorders of osteogenesis and also by intensified osteoclasis. In the case of a disorder of osteogenesis, reduced synthesis of the bone proteins, eg. collagen, elastin, osteocalcin, occurs. There may also be reduced incorporation of calcium and phosphate. Such a diminution of synthesis and/or of incorporation results in osteoporosis or, in some cases, a more intense osteoporosis. Vitamins D and K, for example, are important for protein synthesis and for the incorporation of calcium and phosphate. In the case of osteoclasis, besides calcium, phosphate is also excreted in increased amounts, and in addition the bone proteins decrease. Consequently osteoporosis constitutes a multi-factor phenomenon, with the catabolism of bone mass and the reduction in bone density in the foreground. In this connection the annual rate of catabolism amounts to 1% to 2%; but it may rise to a multiple of this value and becomes dramatic with regard to osteoporosis if it exceeds 3% to 4%. In the case of osteoclasis, calcium, above all, is removed from the bone, which as a result can easily become brittle.

Another disease involving a disorder of bone formation is osteomalacia, which is characterised by deficient incorporation of minerals into the normally or exuberantly formed albumin basic skeleton. This results in broad uncalcified osteoid seams and, accompanied by a general increase in the elastic osteoid substance, greater softness of the bones and a tendency for them to become distorted.

Osteoporosis usually occurs in the sixth decade of life; in men, on account of the greater bone mass and bone density and the continual production of testosterone, it occurs later and far less severely than in women.

Besides the administration of oestrogens as well as highly dosed fluorides in the case of post-menopausal women, in connection with the prophylaxis and therapy of disorders pertaining to bone metabolism and of osteoclasis, use is made above all of calcium and vitamin D, frequently in combination.

For instance, an increase in the daily calcium intake in food from between about 600 and 800 mg to between about 1000 and 1500 mg is recommended, it being possible for these supply quantities to be achieved through increased consumption of milk and milk products. Since milk also contains vitamin D, the supply of vitamin D also rises by this means.

However, since many people do not ingest milk or milk products in sufficient quantities, calcium salts and vitamin D are conventionally ingested in isolated form by way of food supplement or as medicine. By this means the rate of osteoclasis is reduced. Nevertheless, the catabolism progresses, albeit to a lesser extent. It is therefore desirable, besides the administration of calcium and vitamin D, to administer further substances which are as easily digestible as possible and which additionally reduce osteoclasis, characterised by the loss of calcium from the bone.

OBJECT AND SUMMARY OF THE INVENTION

The object underlying the invention is therefore to provide an agent for the prophylaxis and/or therapy of conditions associated with a disorder of bone formation, in particular for influencing osteoclasis. The agent should furthermore have no side-effects and should also be suitable for long-term administration and should be convenient and easy for the patient to take. In addition the agent should also be compatible with other medicaments that may be taken by the patient. Furthermore, the agent according to the invention should be suitable for use by way of food supplement or dietetic foodstuff.

Surprisingly it has now been found that as a result of the intake of potassium citrate and/or potassium lactate and/or potassium malate, especially of potassium citrate and/or potassium lactate, the loss of calcium from the body, and hence osteoclasis, can be reduced. Furthermore it has surprisingly been discovered that a low-dose administration of vitamin K (phylloquinone) has an influence on the metabolism of calcium, to the effect that, by this means, osteoclasis is reduced and the reconstruction of bone is promoted.

DETAILED DESCRIPTION OF THE INVENTION

The subject of the invention is therefore an agent for the prophylaxis and/or therapy of conditions associated with a disorder of bone formation, containing i) potassium citrate, lactate and/or malate, ii) vitamin D and iii) a calcium salt.

The invention further relates to the use of potassium citrate and/or potassium lactate and/or potassium malate together with calcium salts and vitamin D for the prophylaxis and/or therapy of diseases associated with a disorder of bone formation and also of osteoclasis. The invention preferably relates to an agent for the prophylaxis and/or therapy of osteoporosis or osteomalacia.

The named potassium citrates are easily digestible; this is of importance for the reason that osteoclasis, like osteoporosis, is a process which develops slowly and over a long period and which can only be influenced by the long-term application of appropriate substances.

The potassium salts have no side-effects; they are permitted as foodstuff additives and may therefore be employed prophylactically in dietetic foodstuffs or by way of food supplement. In addition they may also be readily processed with regard to taste. This is important, particularly with regard to the necessary prolonged administering.

The potassium citrates or lactates or malates reduce the excretion of calcium in the urine, improve the calcium balance by this means and reduce the rate of catabolism of the bones, since less calcium is released from the bone. In addition they increase osteocalcin, a protein which promotes the construction of bone and hence counteracts the genesis and progression of osteoporosis.

Potassium citrates and lactates are preferred, since in many cases (eg, with simultaneous high blood pressure) the supply of sodium in relatively high quantities is undesirable.

The dosage of the potassium citrates and/or lactates and/or malates amounts ordinarily to 10 mmol to 100 mmol/day, calculated as mmol potassium. 20 to 50 mmol/day are preferred.

As potassium citrates, use may be made of monocitrates, dicitrates and tricitrates of potassium, the tricitrates —eg, tripotassium citrates —being preferred.

The potassium salts should be taken in a mixture with other substances that reduce osteoclasis, such as calcium salts and/or vitamin D.

It is known that vitamin K plays a role in the regulation of bone mineralisation via the formation of the protein osteocalcin. Until now, however, it was supposed that a deficiency of vitamin K practically never occurs and that the additional administering of vitamin K therefore has no influence on bone metabolism.

Surprisingly, according to the invention it has now been found that administering small amounts of vitamin K, namely 50 to 300 $\mu$m/day, reduces osteoclasis. In this connection all forms of vitamin K may be employed. It is best for vitamin K to be used in the form of the easily digestible vitamin $K_1$ (phylloquinone). In this connection it is particularly favourable to administer vitamin $K_1$ together with the potassium salts, calcium salts and vitamin D in order to achieve an optimal effect. In this regard all forms of vitamin D may be employed. However, vitamin $D_3$ (cholecalciferol) is preferred.

The agent according to the invention is administered by oral means and may be formulated in any manner suitable for this method of administering, for example in the form of tablets, capsules, pills, granules or powder to be dissolved. To this end the ingredients are compressed in known manner into tablets, optionally subject to the use of auxiliary substances such as lactose, sucrose, magnesium stearate, talc. Such a preparation is formulated in accordance with galenic instructions that are known per se and subject to incorporation of excipients that are known per se. The agent according to the invention is preferably formulated in a form that is suitable to be dissolved in water.

The potassium salts may be used in the form-of powders to be dissolved in water; they may also be employed in the form of effervescent tablets. In this connection the citrates or lactates are produced in situ, the effervescent tablet containing, for example, potassium hydrogencarbonate and/or sodium hydrogencarbonate and citric acid and/or lactic acid. After the dissolution of the effervescent tablet in water the potassium citrates or lactates are formed by reaction of the hydrogencarbonate with citric acid or lactic acid, respectively. In order to improve the taste, conventional flavourings and aromatic substances may be employed, optionally together with other auxiliary substances such as dyestuffs, stabilisers, sweeteners etc.

The following Examples elucidate the invention in more detail.

EXAMPLES

Example 1

The agent according to the invention was produced by the following substances being intimately mixed with one another:

3.25 g tripotassium citrate (=30 mmol potassium)
4.50 g calcium-L-lactate hydrate (600 mg calcium)
10 $\mu$g vitamin $D_3$ (cholecalciferol)
as well as aromatic substances and saccharin.

The agent was dissolved in water (about 100 to 200 ml) and drunk.

The agent according to the invention was administered daily to a group of ten post-menopausal women for ten days, then 4.50 g calcium-L-lactate hydrate (600 mg calcium) plus 10 $\mu$g vitamin $D_3$ are taken daily by the women for ten days for the purpose of comparison. In both trial periods the excretion of calcium in the urine is measured and hence the calcium balance is drawn up.

Result:

Mixture according to the invention: mean calcium excretion in the urine per day: 203 mg calcium Comparison mixture (without potassium citrate): mean calcium excretion in the urine per day: 265 mg calcium An improvement in the calcium balance by about 60 mg/day. This corresponds to about 20 g calcium per year. Since the human skeletal system contains about 1000 g calcium, the rate of catabolism is therefore reduced by about 2%. In addition, while the agent according to the invention was being taken, osteocalcin (in the serum) increased from 4.8 ng/ml to 5.9 ng/ml, whereas after the comparison preparation had been taken, osteocalcin had fallen to 5.1 ng/ml.

Example 2

The trial of Example 1 was repeated. Two groups of ten post-menopausal women were treated each for one year with either the mixture according to the invention from Example 1 or with calcium lactate plus vitamin $D_3$ (without potassium citrate). After one year the losses of bone in % were determined.

Loss of bone in %

Calcium+vitamin $D_3$: —1.2%

Agent according to the invention: +1.5%

While a loss of bone still occurred with the conventional treatment, with the agent according to the invention it was even possible for an increase in the bone mass to be achieved.

Example 3

The agent according to the invention was produced by the following substances being intimately mixed with one another:

3.25 g tripotassium citrate (=30 mmol potassium)
4.50 g calcium-L-lactate hydrate (600 mg calcium)
10 $\mu$g vitamin $D_3$ (cholecalciferol)
120 $\mu$g vitamin $K_1$ (phylloquinone)
and also aromatic substances and saccharin.

The agent was dissolved in water (about 100 to 200 ml) and drunk.

A group of ten post-menopausal women was now treated, in each case for 14 days, with:

I) 4.50 g calcium-L-lactate hydrate plus 10 $\mu$g vitamin $D_3$ (comparison group)

II) agent according to the invention as specified in Example 1

III) agent according to the invention as specified in Example 3

The following are determined: calcium excretion in the urine, osteocalcin in the serum, hydroxyproline excretion in the urine. (A higher osteocalcin signifies increased osteogenesis, whereas a higher hydroxyproline excretion indicates intensification of osteoclasis.)

|  | Group I | Group II | Group III |
| --- | --- | --- | --- |
| Calcium in the urine | 261 mg | 197 mg | 175 mg |

-continued

|  | Group I | Group II | Group III |
|---|---|---|---|
| (per day): |  |  |  |
| Osteocalcin: | 5.2 ng/ml | 6.2 ng/ml | 7.3 ng/ml |
| Hydroxyproline in the urine (per day): | 30 mg | 27 mg | 24.5 mg |

The results show that the mixture according to the invention as specified in Example 1 (Group II) inhibits osteoclasis and that the additional administration of vitamin $K_1$ (Group III) gives rise to an additional favourable effect with regard to a reduction in osteoclasis.

Example 4

Lozenge tablets were compressed in conventional manner subject to the use of the auxiliary substances talc, magnesium stearate, flavours and saccharin. One tablet contained:

1.50 g tripotassium citrate 2.00 g calcium-L-lactate hydrate

3 µg vitamin $D_3$ (cholecalciferol)

60 µg vitamin $K_1$ (phylloquinone) 10 men aged more than 60 years ingested 3 lozenge tablets daily, in each case over a period of 2 weeks (Group I). After a break of 2 weeks the men took 4.5 g calcium L lactate hydrate plus 9 µg vitamin $D_3$ daily by way of food supplement over a period of 2 weeks (Group II). With the mixture according to the invention (Group I) the average daily calcium balance amounted to +44 mg calcium/day; with the comparison mixture, on the other hand, it amounted to only +5 mg calcium/day.

I claim:

1. A pharmaceutical composition consisting essentially of effective enhancing amounts of (i) potassium citrate, lactate and/or malate, (ii) Vitamin D, (iii) a single calcium salt, and (iv) optionally, Vitamin K, wherein the amounts of (i), (ii), (iii) and (iv), if present, are effective for the prophylaxes and/or therapy of a disorder associated with bone formation, and a pharmaceutically acceptable incipient.

2. The composition of claim 1, wherein said single calcium salt is calcium-L-lactate hydrate.

3. A pharmaceutical composition comprising effective enhancing amounts of (i) potassium citrate, lactate and/or malate, (ii) vitamin D, and (iii) a calcium single salt, in an amount effective for the prophylaxis and/or therapy of conditions associated with a disorder of bone formation, and a pharmaceutically acceptable excipient.

4. A pharmaceutical composition according to claim 3, wherein said composition further comprises vitamin K.

5. A pharmaceutical composition according to claim 3, wherein said single calcium salt is calcium-L-lactate hydrate.

6. A pharmaceutical composition according to claim 3, wherein said composition comprises 10 to 100 mmol potassium citrate or lactate, relative to potassium.

7. A pharmaceutical composition according to claim 6, wherein said composition comprises 5 to 20 mmol tripotassium citrate, corresponding to 15 to 60 mmol potassium.

8. A pharmaceutical composition according to claim 3, wherein (i), (ii), and (iii) are present in amounts effective for the prophylaxis and/or therapy of osteoclasis.

9. The pharmaceutical composition according to claim 3, wherein said composition comprises potassium citrate and/or potassium lactate.

10. The composition according to claim 3, wherein said potassium citrate is selected from the group consisting of monocitrates, dicitrates and tricitrates of potassium.

11. A method for the prophylaxis and/or therapy of conditions associated with a disorder of bone formation in a patient comprising administering to said patient a composition comprising effective enhancing amounts of (i) potassium citrate, lactate and/or malate, (ii) vitamin D, and (iii) a calcium salt, in amounts effective for the prophylaxis and/or therapy of conditions associated with a disorder of bone formation.

12. The method of claim 11, wherein said disorder of bone formation is osteoclasis.

13. The method of treatment according to claim 11, wherein said disorder is osteoporosis or osteomalacia.

14. The method according to claim 11, wherein said potassium citrate, lactate and/or malate is administered in the amount of 10 to 100 mmol/day, relative to potassium.

15. A method according to claim 14, wherein said potassium citrate, lactate and/or malate is administered in the amount of 20 to 50 mmol/day, relative to potassium.

16. The method according to claim 11, further comprising administering vitamin K to a patient in need of such treatment.

17. The method according to claim 16, wherein said vitamin K is administered in the amount 50 to 300 µm/day.

18. The method according to claim 11, wherein said composition is administered orally.

* * * * *